United States Patent

Yamasaki et al.

[11] Patent Number: 6,087,539
[45] Date of Patent: Jul. 11, 2000

[54] PROCESS FOR PRODUCING AN ETHER COMPOUND

[75] Inventors: Hirotaka Yamasaki, Sodegaura; Akihisa Ogawa, Yokkaichi; Shigeru Kamimori, Matsusaka; Yoshikazu Hirao, Yokkaichi; Keiji Fujita, Yokkaichi; Tokuyuki Yoshimoto, Yokkaichi, all of Japan

[73] Assignee: Idemitsu Kosan Co., Ltd., Tokyo, Japan

[21] Appl. No.: 08/930,585

[22] PCT Filed: Apr. 18, 1996

[86] PCT No.: PCT/JP96/01056

§ 371 Date: Oct. 20, 1997

§ 102(e) Date: Oct. 20, 1997

[87] PCT Pub. No.: WO96/33154

PCT Pub. Date: Oct. 24, 1996

[30] Foreign Application Priority Data

Apr. 20, 1995 [JP] Japan .................................. 7-095495

[51] Int. Cl.$^7$ .................................................. C07C 43/11
[52] U.S. Cl. ........................ 568/613; 568/621; 568/672; 568/699
[58] Field of Search .................................. 568/574, 601, 568/613, 672, 699, 606, 621

[56] References Cited

U.S. PATENT DOCUMENTS 2,590,598  3/1952  Copenhaver .......................... 260/615
4,479,017  10/1984  Ayusawa et al. ...................... 568/613

FOREIGN PATENT DOCUMENTS 0 644 175  3/1995  European Pat. Off. .
95/01949  1/1995  WIPO .

*Primary Examiner*—Sreeni Padmanabhan
*Attorney, Agent, or Firm*—Oblon, Spivak, McClelland, Maier & Neustadt, P.C.

[57] ABSTRACT

A process for producing an ether compound represented by the general formula (II) or (III):

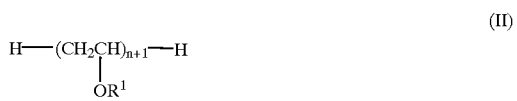

(II)

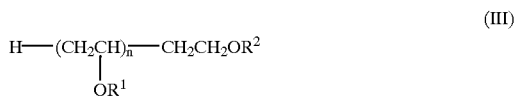

(III)

wherein $R^1$ and $R^2$ represent each an alkyl group or a cycloalkyl group and n represents an integer of 1 to 50, which comprises bringing an acetal compound represented by the general formula (I):

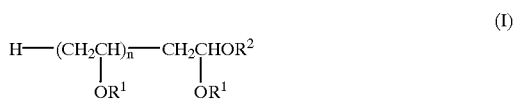

(I)

into reaction with hydrogen in the presence of a solid catalyst comprising (A) nickel in an amount corresponding to 10 to 70% by weight of metallic nickel, and (B) at least one compound selected from the group consisting of oxides of silicon, aluminum, magnesium, titanium, and zirconium; and synthetic or natural inorganic oxides containing one or more of these oxides as the constituents thereof. A vinyl ether polymer having a terminal ether group can be obtained with a good yield without causing corrosion of the apparatus used for the reaction.

16 Claims, No Drawings

PROCESS FOR PRODUCING AN ETHER COMPOUND

This is the U.S. National Stage Application of PCT/LP96/01056 filed Apr. 18, 1996 now WO96/33154 published Oct. 24, 1996.

FIELD OF THE INVENTION

The present invention relates to a process for producing a vinyl ether polymer having a terminal ether group with a good yield without causing corrosion of the apparatus used for the reaction by hydrogenolysis of a vinyl ether polymer having a terminal acetal group in the presence of a catalyst comprising nickel and specific inorganic oxides.

The ether compound produced by the process of the present invention is advantageously used for solvents, adhesives, resins, organic intermediate materials, lubricating oils, insulating oils, and surfactants.

PRIOR ART OF THE INVENTION

As the process for producing an ether from an acetal, for example, a process using a combination of an acid and an alkali metal hydride, a process using a silicon reagent, and a process using diborane, are described in Jikken Kagaku Koza, Volume 20 (the fourth edition, published by Maruzen). However, these processes are not preferred as an industrial process because a stoichiometric amount of an expensive reagent, such as an alkali metal hydride, a silicon reagent, or diborane, is used as the reagent for the hydrogenolysis, and cost of the production is high.

An ether can be produced from an acetal also by catalytic hydrogenolysis in the presence of an acid catalyst. W. L. Howard et al. reported that an ether could be synthesized by catalytic hydrogenolysis of a ketal by using a catalyst containing rhodium supported on alumina in the presence of hydrochloric acid [J. Org. Chem., 26, 1026 (1961)].

As another example of the process for producing an ether from an acetal, a process for producing an ether by catalytic hydrogenolysis of an acetal compound or a ketal compound in the presence of a catalyst in which (1) a halide of an element of the IIIA group of the Periodic Table (aluminum trichloride or boron trifluoride) and (2) platinum or rhodium are supported on a support, is disclosed in Japanese Patent Application Laid-Open No. Showa 54(1979)-135714.

As still another example of the process, a process for producing a glycol ether by hydrogenolysis of a 1,2-alkyl-1,3-dioxorane in the presence of palladium and phosphoric acid or an ester of phosphoric acid is disclosed in Japanese Patent Application Laid-Open No. Showa 58(1983)-189129.

However, when the apparatus used for the reaction is made of an ordinary material, these processes has a problem that corrosion of the apparatus takes place because an acidic cocatalyst, such as hydrochloric acid, aluminum trichloride, boron trifluoride, and phosphoric acid, is used. A complicated step is also necessary for removing the cocatalyst from the product. Therefore, these processes are not advantageous.

A process for producing an ether from an acetal by hydrogenolysis in the absence of an acid catalyst is also known. A process for producing a dialkyl glycol ether by hydrogenolysis of a formal of a glycol ether in the presence of a catalyst comprising nickel, cobalt, or copper is disclosed in Japanese Patent Application Laid-Open No. Showa 51(1976)-36106.

A process for producing a dialkyl glycol ether by hydrogenolysis of an acetal in the presence of a catalyst comprising nickel, molybdenum, and/or rhenium is disclosed in Japanese Patent Application Laid-Open No. Showa 56(1981)-71031.

In a report cited by M. Verzele et al. in their report [J. Chem. Soc., 5598 (1963)], an ether is produced by hydrogenolysis of an acetal in the presence of a nickel-kieselguhr catalyst. However, this process relates to hydrogenolysis of a low molecular weight acetal.

In the processes described above, the object compound is a low molecular weight compound. No process for producing a vinyl ether polymer having a terminal ether group by hydrogenolysis of a vinyl ether polymer having a terminal acetal group is disclosed in the above references.

A process for producing a vinyl ether polymer having a terminal ether group by hydrogenolysis of a vinyl ether polymer having a terminal acetal group is disclosed in U.S. Pat. No. 2,590,598. This process has the object of providing an ether compound represented by the following general formula (V):

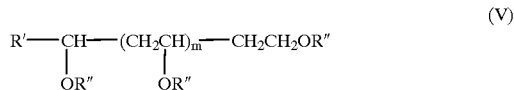

wherein R' and R" represent each a hydrocarbon group selected from alkyl groups, aryl groups, and aralkyl groups, and m represents an integer of 0 to 10, by hydrogenolysis of a polyoxyacetal represented by the following general formula (IV):

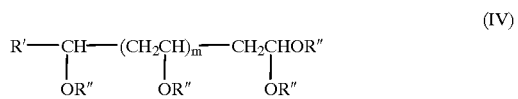

wherein R', R", and m are the same as those described above, in the presence of a metal catalyst for hydrogenation under a pressure of at least; 1000 lb/in$^2$ (68 kg/cm$^2$) at a temperature of 160° C. or higher under a neutral or basic condition.

In the specification of the above patent, the catalyst is specified only as a metal catalyst for hydrogenation. Raney nickel alone was used in the examples. The yield of the product was as low as 52%.

Production of an ether compound by hydrogenation of an acetal or a ketal in the presence of a combination of a solid hydrogenation catalyst and a solid acid catalyst is described in International Patent Application Laid-Open No. WO 93/24435 and Japanese Patent Application Laid-Open No. Heisei 6(1994)-128184. However, when water is not completely removed from the reaction system because of the interaction with the solid catalyst, side reactions such as hydrolysis of the terminal acetal group in the starting material and formation of by-products such as alcohols by the hydrogenation take place because a combination of a solid hydrogenation catalyst and a solid acid catalyst is used. Therefore, the amount of water contained in the materials and the catalyst components must be rigorously restricted. Furthermore, steps for separation and recovery of the catalysts must be included in the process for industrial application of the process because the two types of catalyst component are mixed, and this requirement makes the process more complicated. The yield of the reaction is not satisfactory.

As described above, no industrially advantageous process for producing a vinyl ether polymer having a terminal ether group by hydrogenolysis of a vinyl ether polymer having a terminal acetal group has heretofore been proposed.

Therefore, it is industrially important to provide a process for producing a vinyl ether polymer having a terminal ether group by hydrogenolysis of a vinyl ether polymer having terminal acetal group with sufficient reactivity and good selectivity without causing corrosion of the apparatus used for the reaction.

It is generally known that reactions such as hydrogenolysis do not procieed easily with a compound of a high molecular weight. This knowledge can also be applied to the compound represented by the general formula (I) which is the object compound of the present invention and will be described later. Achieving the complete hydrogenolysis with the compound represented by the general formula (I) under ordinary conditions is more difficult than achieving the complete hydrogenolysis with aliphatic acetals of a low molecular weight. When an ether compound which is obtained by the hydrogenolysis of an acetal compound but still contains remaining starting materials is used in various applications, expected properties are often not exhibited. For example, viscosity, adhesive property, electric properties, and heat stability tend to become different from the expected properties. These properties also tend to change with time and to show markedly inferior stability during the use. These tendencies are considered to arise by the change of the acetal group remaining at the end into other structures under the condition of the use. It is well known that an acetal group is converted into an aldehyde, an alcohol, an acid, or an unsaturated ether under various conditions.

To achieve the complete hydrogenolysis of a polymeric material having a low reactivity, it is generally necessary that the reaction be conducted under a severe condition by adjusting the conditions of the reaction such as the temperature and the pressure. However, because the compound represented by the general formula (I) used as the stariting material has many alkoxy groups in the molecule, it is necessary to avoid a severe condition which causes side reactions, such as elimination of other alkoxy groups and isomerization of the structure, in addition to the desired reaction of the acetal group.

Therefore, it is important for solving the problems described above 1) that an acetal compound of a high molecular weight which has a low reactivity is converted into an ether compound with a good yield, and 2) that the desired ether compound is selectively produced by suppressing the formation of by-products.

SUMMARY OF THE INVENTION

Accordingly, the object of the present invention is to provide a process for producing a vinyl ether polymer having a terminal ether group by hydrogenolysis of a vinyl ether polymer having terminal acetal group with sufficient reactivity and good selectivity and without causing corrosion of the apparatus used for the reaction.

As the result of extensive studies undertaken by the present inventors, it was discovered that the above object can be achieved by hydrogenolysis of an acetal compound in the presence of a catalyst comprising nickel and specific inorganic oxides. The present invention was completed on the basis of the discovery.

The present invention provides a process for producing an ether compound represented by the general formula (II) or (III):

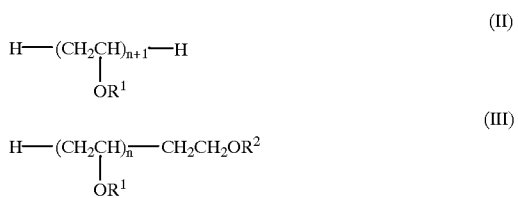

wherein $R^1$ and $R^2$ represent each an alkyl group or a cycloalkyl group and may be the same or different, $R^1$ in a plurality of repeating units may the same or different, and n represents an integer of 1 to 50, which comprises bringing an acetal compound represented by the general formula (I):

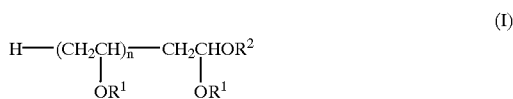

wherein $R^1$, $R^2$, and n are the same as those in the formulae (II) and (III), into reaction with hydrogen in the presence of a solid catalyst comprising (A) nickel in an amount corresponding to 10 to 70% by weight of metallic nickel, and (B) at least one compound selected from the group consisting of oxides of silicon, aluminum, magnesium, titanium, and zirconium; and synthetic or natural inorganic oxides containing one or more of these oxides as the constituents thereof.

DETAILED DESCRIPTION OF THE INVENTION

The present invention is described in more detail in the following. The compound represented by the general formula (I) is referred to as compound (I) hereinafter. The compounds represented by the general formulae (II) and (III) are also referred to as compound (II) and compound (III), respectively.

The catalyst used in the present invention is a solid catalyst comprising nickel and at least one compound selected from the group consisting of oxides of silicon, aluminum, magnesium, titanium, and zirconium; and synthetic or natural inorganic oxides containing one or more of these oxides as the constituents thereof. The catalyst contains nickel in an amount corresponding to 10 to 70% by weight of metallic nickel. As the oxide, silica, alumina, magnesia, titania, or zirconia is preferably used. As the synthetic or natural inorganic oxide containing one or more of these oxides as the constituents thereof, silica-alumina, silica-magnesia, zeolite, activated clay, or diatomaceous earth is preferably used. Specific examples of the solid catalyst preferably used in the present invention include nickel-silica-alumina catalysts, nickel-alumina catalysts, nickel-silica-alumina-magnesia catalysts, nickel-zircDnia catalysts, and nickel-diatomaceous earth catalysts. The solid catalyst may be used singly or as a combination of two or more types.

In the present invention, nickel and the oxide may be simply mixed and used as the catalyst. However, the catalyst is preferably prepared by supporting nickel on the oxide, or by mixing nickel and the oxide well by a method such as kneading, followed by molding the resultant mixture into a solid form. It is particularly important for achieving the object of the present invention that the two components of the catalyst are present within the same catalyst in the solid form and are always present in the vicinity of each other during the reaction. The nickel component of the catalyst may be present in the catalyst as the metal or as an oxide. It is necessary for increasing the yield of the reaction and decreasing the formation of by-products that the nickel component be contained in an amount corresponding to 10 to 70% by weight, preferably 15 to 65% by weight, of metallic nickel. When the content of nickel in the catalyst is more than the specified range, the complete hydrogenolysis of the terminal acetal group in the molecule of the starting material cannot be achieved, and the amount of by-products increases. When the content of nickel in the catalyst is less than the specified range, the hydrogenolysis of the acetal is incomplete. The by-products formed in the above are considered to be compounds formed by partial scission of the methylene chain, compounds formed by elimination of alkoxy groups which are not included in the acetal group, and compounds formed when these reactions take place consecutively.

The process for preparation of the solid catalyst used in the present invention is not particularly limited. The catalyst comprising nickel and the oxide can be prepared in accordance with various processes, such as the supporting process, the co-precipitation process, the ion-exchange process, the process of synthesis in the solid phase, and the mixing process. Commercial catalysts may also be used without additional treatments when the requirements disclosed in the present invention are satisfied.

In an example of the process for preparation of the catalyst, an aqueous solution containing a compound which is decomposed by reduction to form metallic nickel, such as nickel nitrate, nickel formate, and basic nickel carbonate, is neutralized to form precipitates. The formed precipitates are kneaded with a support selected from oxides, such as silica, silica-alumina, alumina, magnesia, titania, and zirconia, and the mixture is dried. The dried mixture is molded and then treated under a reducing atmosphere to obtain a catalyst. In another example of the process, a nickel salt used as the starting material, such as those described above, is dissolved in a solvent such as water, and then supported on a support selected from the oxides described above in accordance with a conventional process. The supported material thus prepared is dried and reduced to obtain a catalyst.

Preferable examples of the alkyl group represented by $R^1$ or $R^2$ in the general formulae (I), (II), and (III) include linear or branched alkyl groups having 1 to 8 carbon atoms, such as methyl group, ethyl group, propyl group, isopropyl group, butyl group, isobutyl group, pentyl group, isopentyl group, hexyl group, isohexyl group, heptyl group, isoheptyl group, octyl group, and isooctyl group. Preferable examples of the cycloalkyl group represented by $R^1$ or $R^2$ in the general formulae (I), (II), and (III) include cycloalkyl groups having 3 to 8 carbon atoms, such as cyclopropyl group, cyclobutyl, cyclopentyl group, cyclohexyl group, cycloheptyl group, and cyclooctyl group.

In an example of preparation of compound (I) used as the starting material, an alkyl vinyl ether represented by the following general formula (VI):

$$CH_2=CHOR^1 \qquad (VI)$$

is polymerized in the presence of an acetal represented by the general formula (VII):

$$CH_3CH(OR^2)_2 \qquad (VII)$$

In the above formulae, $R^1$ and $R^2$ are the same as those described above. Compound (I) can also be prepared by other conventional processes.

Generally in preparation of a polymer of a high molecular weight, a polymer having a uniform molecular weight is difficult to obtain. Instead, a mixture of polymers having molecular weights distributed in a range is generally obtained. Compound (I) used as the starting material in the present invention can include this mixture of polymers. Compound (I) used as the starting material in the present invention can also include compounds obtained by copolymerization of vinyl ethers having different types of $R^1$.

The hydrogenolysis in the process of the present invention can be conducted in accordance with the same process as a conventional hydrogenolysis process. The hydrogenolysis may be conducted in accordance with a continuous process or a batch process. The catalyst may be used in accordance with a suspended bed process or a fixed bed process. A process in which compound (I) used as the starting material is continuously supplied to a reactor packed with a catalyst in combination with hydrogen to allow the reaction to proceed and then compound (II) and compound (III) formed by the reaction are recovered, i.e. continuous reaction in accordance with a fixed bed process, is preferable because the formation of isomers is decreased and the selectivity is increased.

The hydrogenolysis reaction can also be conducted effectively in accordance with a suspended bed process, i.e. in the presence of a solid catalyst in a suspended condition.

A temperature of the reaction selected in the range of 70 to 200° C., preferably 90 to 190° C., is preferred for further enhancing the advantages of the present invention. When the temperature is lower than the specified range, the desired hydrogenolysis reaction does not proceed sufficiently. When the temperature is higher than the specified range, the by-products described above increase. The reaction is conducted under a pressure of 3 to 80 kg/cm$^2$G, preferably 3 to 60 kg/cm$^2$G.

When the reaction is conducted in accordance with a batch process, other reaction conditions can be decided suitably. The amount of the catalyst and the time of the reaction can be decided so that all the starting material is consumed at the selected temperature under the selected pressure. The concentration of the catalyst can be selected in the range of 0.01 to 20% by weight, preferably 0.1 to 15% by weight, of the starting material.

The catalyst recovered from the reaction product by filtration or decantation can be used again.

When the reaction is conducted in accordance with a continuous process such as a fixed bed process, the LHSV [the liquid hourly space velocity which is defined as (flow rate of the introduced compound (I), ml/hr)/(amount of the solid catalyst, ml)] of compound (I) used as the starting material is in the range of 0.01 to 10 hr$^{-1}$, preferably 0.05 to 5 hr$^{-1}$. The GHSV [the gas hourly space velocity which is defined as velocity of the introduced hydrogen gas, mlhr)/ (amount of the solid catalyst, ml)] is in the range of 5 to 1000 hr$^{-1}$, preferably 10 to 500 hr$^{-1}$. The ratio in mol of hydrogen gas to compound (I) is 2 to 3000, preferably 10 to 1000.

In the process of the present invention, compound (I) used as the starting material may be used directly in the reaction. However, compound (I) is preferably diluted with a suitable solvent to reduce the viscosity when compound (I) has a high molecular weight. Example of the solvent used for the dilution include alcohols such as methanol and ethanol, ethers such as glycol ethers, tetrahydrofuran, and dioxane, linear or branched aliphatic or aromatic hydrocarbons such as hexane, heptane, octane, nonane, benzene, toluene, and xylene. Aliphatic hydrocarbons are preferably used.

Compound (II) and compound (III) which are the object compounds of the process of the present invention can be isolated by removal of the catalyst from the reaction product described above by filtration or decantation, followed by necessary treatments such as distillation, extraction, washing, and drying.

The number of the repeating unit (i.e. the degree of polymerization) in Compound (II) and compound (III) obtained in accordance with the process of the present invention can be suitably selected in accordance with the desired kinematic viscosity. The number of the repeating unit is generally selected in such a manner that the kinematic viscosity at 40° C. is preferably 5 to 1,000 cSt, more preferably 7 to 300 cSt. The average molecular weight of compound (II) and compound (III) is generally 150 to 2,000. Compound (II) or compound (III) having a kinematic viscosity outside the range described above may also be used by mixing with another compound having a suitable kinematic viscosity in such a manner that the kinematic viscosity of the resultant mixture is adjusted to a value within the range described above.

According to the present invention, a vinyl ether polymer having a terminal ether group can be produced by hydrogenolysis of a vinyl ether polymer having a terminal acetal group in the presence of a catalyst comprising nickel and specific inorganic oxides with a good yield without causing problems such as corrosion of the apparatus used for the reaction.

The ether compound produced in accordance with the present invention is advantageously used for solvents, adhesives, resins, organic intermediate materials, lubricating oils, insulating oils, and surfactants.

The present invention is described more specifically with reference to examples, comparative examples, and reference examples in the follwing.

REFERENCE EXAMPLE 1 (Preparation and analysis of catalysts)

(1) Nickel-silica-alumina Catalyst (catalyst-1)

To an aqueous solution containing 600 g of nickel nitrate ($Ni(NO_3)_2 \cdot 6H_2O$), a solution prepared by dissolving 500 g of ammonium hydrogencarbonate (($NH_4$)$HCO_3$) into 2000 ml of ion-exchanged water was added under vigorous stirring to neutralize the solution. The resultant solution was left standing until the formed precipitates were settled down. The precipitates were separated by filtration and washed, and the obtained cake was dried.

To 170 g of the cake obtained above, 5 g of silica-alumina (alumina, 13% ) produced by Nikki Kagaku Co., Ltd. was added as the support. The components were thoroughly mixed with a kneader together with 50 ml of ion-exchanged water. The resultant mixture was dried and molded into pellets of 4 mm×3 mm. The obtained pellets were reduced with hydrogen in a glass reaction tube while the reaction tube was heated to the maximum temperature of 400° C. After the reduction was finished, the reaction tube was purged with nitrogen, and cooled to a room temperature. Then, the air was slowly introduced into the reaction tube to stabilize the product by oxidation. The amount of the air was controlled so that the maximum temperature did not exceed 50° C. The stabilized nickel-silica-alumina catalyst contained about 49% by weight of nickel.

(2) Nickel-alumina Catalyst (catalyst-2)

Nickel nitrate ($Ni(NO_3)_2 \cdot 6H_2O$) in an amount of 280 g and aluminum nitrate ($Al(NO_3)_3 \cdot 9H_2O$) in an amount of 120 g were dissolved in pure water to prepare 640 ml of a solution. By diluting 320 g of a 25% aqueous solution of NaOH with pure water, 750 ml of another solution was separately prepared. In a vessel equipped with a stirrer, 200 ml of pure water was placed and heated to 60° C. The two solutions prepared above were simultaneously added dropwise into the vessel, and a neutralized the solution was obtained. The temperature of the content in the vessel was controlled so that the maximum temperature was kept at or lower than 70° C. After the addition of the two solutions was finished, the resultant product was aged. The formed precipitates were separated by filtration and washed with pure water until the nitrate ion was not detected. The obtained wet cake (600 to 700 ml) was dried under a nitrogen stream at 110° C. Then, the temperature was increased to 350° C. and the dried cake was decomposed at this temperature for 5 to 8 hours. To the powder of the catalyst (about 110 g) obtained above, 2% of graphite was added, and the mixture was molded into pellets of 4 mm×3 mm. The obtained pellets were placed in a glass reaction tube. The temperature of the reaction tube was slowly increased to the maximum temperature of 400° C. The pellets were reduced with hydrogen at this temperature. After the reduction was finished, the reaction tube was purged with nitrogen and cooled to a room temperature. Then, the air was slowly introduced into the glass tube to stabilize the product by oxidation. The amount of the air was controlled so that the maximum temperature did not exceed 50° C. The stabilized nickel-alumina catalyst contained about 44% by weight of nickel and had a specific surface area of 180 $m^2/g$.

(3) Nickel-silica-alumina-magnesia catalyst (a commercial catalyst) (catalyst-3)

A nickel-silica-alumina catalyst which was produced by N. E. Chemcat Company and molded to 3/64 inches by injection was used. The elemental analysis of the catalyst showed that the catalyst contained 57% by weight of nickel, 0.5% by weight of aluminum, 6.5% by weight of silicon, and 0.04% by weight of magnesium. It was also confirmed that aluminum and silicon were present in the form of oxides. The catalyst had a specific surface area of 230 $m^2/g$.

(4) Nickel-zirconia Catalyst (catalyst-4)

Nickel nitrate ($Ni(NO_3)_2 \cdot 6H_2O$) in an amount of 60 g was dissolved in 50 ml of pure water. The obtained solution was divided into two parts and then allowed to be absorbed successively into 80 g of a zirconium oxide catalyst produced by Strem Company (molded into 3 mm×3 mm). The product was dried by a rotary evaporator and then placed in a glass reaction tube. The product in the reaction tube was slowly heated under a nitrogen stream and baked at 350° C. for 7 hours. After the reaction tube was cooled, the nitrogen stream was replaced with a stream of hydrogen diluted with nitrogen. A preliminary reduction was conducted under this stream at 400° C. The reaction tube was purged with nitrogen and cooled to a room temperature. Then, the air was slowly introduced into the reaction tube to stabilize the product by oxidation. The amount of the air was controlled so that the maximum temperature did not exceed 50° C. The stabilized nickel-zirconia catalyst contained about 17% by weight of nickel and had a specific surface area of 80 $m^2/g$.

(5) Nickel-silica-alumina Catalyst (a commercial catalyst) (catalyst-5)

A molded product of a nickel-silica-alumina catalyst produced by Nikki Kagaku Co., Ltd. was used. The elemental analysis of the catalyst showed that the catalyst contained 52% by weight of nickel, 9% by weight of alumina, and 16% by weight of silica.

REFERENCE EXAMPLE 2 (Preparation of polyethyl vinyl ether having a terminal acetal group)

A 5 liter glass flask equipped with a dropping funnel, a cooler, and a stirrer was charged with 1000 g of toluene, 500 g of acetaldehyde diethylacetal, and 5.0 g of boron trifluoride diethyl etherate. Ethyl vinyl ether in an amount of 2500 g was placed in the dropping funnel and added dropwise into the flask in 2 hours and 30 minutes. The reaction started during the addition, and the temperature of the reaction solution increased. The temperature of the reaction solution was kept at about 25° C. by cooling with an ice water bath. After the addition was finished, the reaction solution was stirred for further 5 minutes. Then, the reaction mixture was transferred to a washing vessel and washed with 1000 ml of a 5% aqueous solution of sodium hydroxide three times and then with 1000 ml of water three times. The solvent and the remaining starting materials were removed under a vacuum to obtain 2833 g of a product. The result of the $^1$H-NMR analysis showed that the main component of the product was compound (I) in which both $R^1$ and $R^2$ were ethyl groups. The results of analyses by the gas chromatography and the gel chromatography showed that the product was a mixture of the compounds in which n was 1 to 20. The kinematic viscosity of the product was measured by a Cannon-Fenske viscometer to obtain kinematic viscosities of 5.18 cSt at 100° C. and 38.12 cSt at 40° C.

REFERENCE EXAMPLE 3 (Preparation of a vinyl ether copolymer having a terminal acetal group)

A 5 liter glass flask equipped with a dropping funnel, a cooler, and a stirrer was charged with 1000 g of toluene, 400 g of acetaldehyde diethylacetal, and 4.5 g of boron trifluoride diethyl etherate. Ethyl vinyl ether in an amount of 1600 g and isobutyl vinyl ether in an amount of 2200 g were placed in the dropping funnel and added dropwise into the flask in 4 hours. The reaction started during the addition, and the temperature of the reaction solution increased. The temperature of the reaction solution was kept at about 25° C. by cooling with an ice water bath. After the addition was finished, the reaction solution was stirred for further 5 minutes. Then, the reaction mixture was transferred to a washing vessel and washed with 1000 ml of a 5% aqueous solution of sodium hydroxide three times and then with 1000 ml of water three times. The solvent and the remaining starting materials were removed under a vacuum to obtain 3960 g of a product. The result of the $^1$H-NMR analysis showed that the main component of the product was compound (I) in which $R^1$ in some repeating units was ethyl group, $R^1$ in the other repeating units was isobutyl group, and both $R^1$ and $R^2$ in the terminal group were ethyl groups. The product was estimated to be a mixture of compounds having various molecular weights. The kinematic viscosity of the product was 112.5 cSt at 40° C.

EXAMPLE 1 (Hydrogenolysis of a vinyl ether polymer having a terminal acetal group)

The vinyl ether polymer having a terminal acetal group prepared in Reference Example 2 was diluted with the same volume of n-hexane, and the obtained solution was used as the starting material of the hydrogenolysis. A pressure-resistant reaction tube of 25 mm inner diameter having an outer jacket made of SUS316 was used as the reactor. The temperature of the reaction was controlled by passing heated silicone oil through the jacket.

The nickel-silica-alumina catalyst prepared in Reference Example 1 (catalyst 1) was packed into the reactor. The reaction was allowed to proceed at a reaction temperature of 140° C. under a reaction pressure of 20 kg/cm$^2$G. The flow rate of the ethyl vinyl ether oligomer diluted with n-hexane was 30 ml/hr (LHSV including n-hexane=0.3 hr$^{-1}$), and the flow rate of hydrogen gas was 12 normal liter/hr (GHSV= 120 hr$^{-1}$).

The solution of the reaction product was separated, and n-hexane used as the solvent and ethanol formed by the reaction were removed under a vacuum. The result of the $^1$H-NMR analysis showed that the product was compound (II) or compound (III) in which both $R^1$ and $R^2$ were ethyl groups (compound (A)). The conversion of the reaction was 100%, and the selectivity of compound (A) was 92%. The conversion was obtained by the $^1$H-NMR analysis of a sample adjusted to a specified concentration. In the analysis, the integration curve of the methine proton (4.8 ppm) was expanded 1000 times and compared with the corresponding result of the starting material which was set to 100%. The selectivity is the fraction of the compound which was not isomerized by the hydrogenolysis but remained in the structure of compound (A), and was obtained from integrated values of related curves in the gas chromatography chart. The product had a kinematic viscosity of 27.6 cSt at 40° C.

EXAMPLES 2 TO 6 AND COMPARATIVE EXAMPLES 1 TO 3 (Reaction by using catalysts having various nickel contents)

Nickel-silica-alumina catalysts having various nickel contents were prepared in accordance with the same procedures as those used for the preparation of catalyst-1 in Reference Example 1. Hydrogenolysis reaction was conducted by using these catalysts under the conditions shown in Table 1.

The reactor used in Example 1 was charged with 100 ml of one of the catalysts containing 4%, 16%, 28%, and 49% of nickel. The vinyl ether polymer having a terminal acetal group prepared in Reference Example 2 (viscosity 42.2 cSt) was diluted with the same volume of isooctane, and the obtained solution was fed into the catalyst layer at a flow rate of 30 mn/hr (LHSV including isooctane=0.3 hr$^{-1}$). The flow rate of hydrogen gas was 12 normal liter/hr (GHSV=120 hr$^{-1}$).

The reaction was conducted at various temperatures under various pressures. The conversion and the selectivity were obtained by the same methods as those in Example 1. The results of the reaction are shown in Table 1.

TABLE 1

|  | content of nickel (% by wt) | reaction temperature (° C.) | reaction pressure (kg/cm$^2$) | conversion (%) | selectivity (%) | kinematic viscosity (cSt) |
|---|---|---|---|---|---|---|
| Example 2 | 16 | 140 | 20 | 94 | 91 | 35.3 |
| Example 3 | 16 | 180 | 25 | 99 | 85 | 33.8 |
| Example 4 | 28 | 130 | 20 | 95 | 93 | 34.5 |
| Example 5 | 28 | 150 | 20 | 100 | 91 | 33.2 |
| Example 6 | 49 | 150 | 7 | 100 | 89 | 32.2 |

TABLE 1-continued

|  | content of nickel (% by wt) | reaction temperature (° C.) | reaction pressure (kg/cm²) | conversion (%) | selectivity (%) | kinematic viscosity (cSt) |
|---|---|---|---|---|---|---|
| Comparative Example 1 | 4 | 150 | 20 | 63 | 45 | 40.1 |
| Comparative Example 2 | 4 | 150 | 40 | 70 | 72 | 39.4 |
| Comparative Example 3 | 4 | 180 | 20 | 85 | 64 | 38.1 |

EXAMPLES 7 TO 19 (Reaction by using various types of catalyst)

One of the catalysts prepared in Reference Example 1 (catalyst-2 to catalyst-5) was packed into the reactor used in Example 1 in an amount shown in Table 2. The condition of the catalyst was adjusted as shown in Table 2. The polyethyl vinyl ether having a terminal acetal group prepared in Reference Example 2 was diluted with the same volume of isooctane, and a specified amount of the obtained solution was fed into the catalyst layer in combination with hydrogen.

The conversion and the selectivity were obtained by the same methods as those in Example 1. The results of the reaction are shown in Table 2.

the reaction pressure of 20 kg/cm². The flow rate of hydrogen gas was 12 normal liter/hr (GHSV=120 hr$^{-1}$). The conversion of the starting material was 16% when the reaction was conducted at a temperature of 130° C., and 57% when the reaction was conducted at a temperature of 180° C. In both cases, the selectivity of the ether compound which was the object compound was 0%.

EXAMPLE 20 (Hydrogenolysis of a vinyl ether copolymer having a terminal acetal group)

Into the reactor used in Example 1, 100 ml of a nickel-silica-alumina-magnesia catalyst (catalyst 3) prepared in Reference Example 1 was packed. The polyethyl vinyl ether having a terminal acetal group prepared in Reference Example 3 was diluted with the same volume of isooctane,

TABLE 2

|  | catalyst | reaction temperature (° C.) | reaction pressure (kg/cm²) | SV of material (hr$^{-1}$) | SV of hydrogen (hr$^{-1}$) | conversion (%) | selectivity (%) |
|---|---|---|---|---|---|---|---|
| Example 7 | 2 | 140 | 7 | 0.3 | 120 | 98 | 92 |
| Example 8 | 2 | 160 | 20 | 0.3 | 120 | 100 | 85 |
| Example 9 | 2 | 150 | 7 | 0.6 | 120 | 99 | 89 |
| Example 10 | 2 | 140 | 20 | 0.3 | 120 | 100 | 82 |
| Example 11 | 3 | 120 | 20 | 0.3 | 120 | 89 | 88 |
| Example 12 | 3 | 160 | 20 | 0.6 | 120 | 95 | 86 |
| Example 13 | 4 | 150 | 20 | 0.3 | 120 | 91 | 77 |
| Example 14 | 4 | 150 | 40 | 0.2 | 90 | 98 | 79 |
| Example 15 | 4 | 170 | 20 | 0.2 | 90 | 100 | 73 |
| Example 16 | 5 | 140 | 3 | 0.6 | 120 | 96 | 70 |
| Example 17 | 5 | 140 | 5 | 0.6 | 120 | 97 | 82 |
| Example 18 | 5 | 140 | 8 | 1.0 | 120 | 91 | 83 |
| Example 19 | 5 | 140 | 20 | 0.8 | 120 | 94 | 90 |

$$SV \text{ of material (hr}^{-1}) = \frac{\text{flow rate of the starting material (including the solvent), ml/hr}}{\text{amount of the catalyst, ml}}$$

$$SV \text{ of hydrogen (hr}^{-1}) = \frac{\text{flow rate of hydrogen, ml/hr}}{\text{amount of the catalyst, ml}}$$

COMPARATIVE EXAMPLE 4 (Reaction using a ruthenium catalyst)

A 2% ruthenium/carbon catalyst produced by N. E. Chemcat Company (3 to 8 mesh) in an amount of 50 ml and silica-alumina produced by Tomita Seiyaku Co., Ltd. (Tomix AD700; silica:alumina=10:1) in an amount of 50 ml were mixed with each other, and the obtained mixture was packed into the reactor used in Example 1.

The polyethyl vinyl ether having a terminal acetal group prepared in Reference Example 2 was diluted with the same volume of n-hexane, and the obtained solution was fed into the catalyst layer at a flow rate of 30 ml/hr (LHSV including the solvent=0.3 hr$^{-1}$) in combination with hydrogen under and the obtained solution was continuously fed into the catalyst layer at a flow rate of 30 ml/hr (LHSV including the solvent =0.3 hr$^{-1}$) in combination with hydrogen at a reaction temperature of 160° C. under the reaction pressure of 7 kg/cm². The flow rate of hydrogen gas was 8 normal liter/hr (GHSV=80 hr$^{-1}$).

The reaction product was analyzed by $^1$H-NMR after the solvent was removed by distillation. The conversion was 100%, and the kinematic viscosity of the product was 68.2 cSt at 40° C.

EXAMPLE 21 (Hydrogenolysis in accordance with a batch process)

A 1 liter autoclave made of SUS316L was charged with 9.0 g of a nickel-diatomaceous earth catalyst (a product of Nikki Kagaku Co., Ltd.; N113) and 300 g of the vinyl ether copolymer having a terminal acetal group prepared in Reference Example 3. The autoclave was purged with hydrogen, and the pressure of hydrogen was increased to 35 kg/cm²G. The temperature of the autoclave was increased to 140° C., and the reaction was allowed to proceed at this temperature for 2 hours. During the period of increase in the temperature and during the reaction, decrease in the pressure was observed because of the reaction, and the reaction pressure was kept at 35 kg/cm²G by additional introduction of hydrogen from time to time.

The catalyst was removed from the reaction product by filtration, and volatile components were removed by distillation. The resultant reaction product was analyzed by the ¹H-NMR, and the conversion was found to be 100%. The yield of the reaction product was 271.5 g (90.5% by weight based on the vinyl ether copolymer having a terminal acetal group used as the starting material). The kinematic viscosity was 88.3 cSt at 40° C.

EXAMPLE 22

A 1 liter autoclave made of SUS316L was charged with 9.0 g of a nickel-silica-alumina catalyst (a product of N. E. Chemcat Company; content of the supported nickel, 57% by weight) and 300 g of the vinyl ether copolymer having a terminal acetal group prepared in Reference Example 3. The autoclave was purged with hydrogen, and the pressure of hydrogen was increased to 35 kg/cm²G. The temperature of the autoclave was increased to 140° C., and the reaction was allowed to proceed at this temperature for 2 hours. During the period of increase in the temperature and during the reaction, decrease in the pressure was observed because of the reaction, and the reaction pressure was kept at 35 kg/cm²G by additional introduction of hydrogen from time to time.

The catalyst was removed from the reaction product by filtration, and volatile components were removed by distillation. The resultant reaction product was analyzed by the ¹H-NMR, and the conversion was found to be 100%. The yield of the reaction product was 270.0 g (90.0% by weight based on the vinyl ether copolymer having a terminal acetal group used as the starting material). The kinematic viscosity was 89.0 cSt, at 40° C.

COMPARATIVE EXAMPLE 5

(1) Raney nickel which had been developed (a product of Kawaken Fine Chemical Co., Ltd.; M300T) (in the condition containing water) in an amount of 100 g was placed in a flask. The supernatant fluid was removed, and 200 g of anhydrous ethanol was added to the remaining catalyst. The mixture was stirred well and then left standing. The supernatant fluid was removed. Anhydrous ethanol in an amount of 200 g was added again to the remaining catalyst, and the mixture was stirred well. This operation was repeated five times.

(2) Zeolite (a product of Toso Co., Ltd.; HSZ330HUA) in an amount of 30 g was dried in a vacuum oven at 150° C. for 1 hour. During the drying, the pressure of the vacuum oven was kept decreased by using an oil rotation vacuum pump.

(3) A 1 liter autoclave made of SUS316L was charged with 9 g of Raney nickel which had been developed and prepared in (1) described above, 200 g of hexane, 9 g of zeolite obtained in (2) described above, and 15 g of acetaldehyde diethylacetal. The autoclave was purged with hydrogen. Then, the pressure of hydrogen was kept at 35 kg/cm²G, and the temperature was increased to 130° C. in 30 minutes under stirring. The reaction was allowed to proceed at 130° C. for further 30 minutes. After the reaction was finished, the reaction product was cooled to a room temperature, and then the pressure was released to an atmospheric pressure. The reaction product was left standing for 30 minutes to allow the catalyst to precipitate, and the reaction solution was removed by decantation.

(4) Into the 1 liter autoclave made of SUS316L containing 9 g of Raney nickel which had been developed and 9 g of zeolite as described above, 300 g of the vinyl ether polymer having a terminal acetal group prepared in Reference Example 3 was placed. The autoclave was purged with hydrogen. Then, the pressure of hydrogen was kept at 35 kg/cm²G, and the temperature was increased to 140° C. in 30 minutes under stirring. The reaction was allowed to proceed at 140° C. for further 2 hours. During the period of increase in the temperature and during the reaction, decrease in the pressure was observed because of the reaction, and the reaction pressure was kept at 35 kg/cm²G by additional introduction of hydrogen from time to time.

The catalyst was removed from the reaction product by filtration, and volatile components were removed by distillation. The resultant reaction product was analyzed by the ¹H-NMR, and the conversion was found to be 100%. The yield of the reaction product was 247.2 g (82.4% by weight based on the vinyl ether polymer having a terminal acetal group used as the starting material). The kinematic viscosity was 90.2 cSt at 40° C.

What is claimed is:

1. A process for producing an ether compound having the formula (II) or (III):

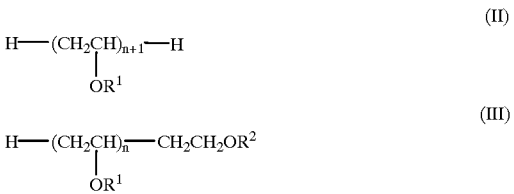

wherein $R^1$ and $R^2$ each represent alkyl or cycloalkyl and are the same or different, $R^1$ in a plurality of repeating units is the same or different, and n represents an integer of 2 to 32, which comprises reacting one or more acetal compounds having the formula (I):

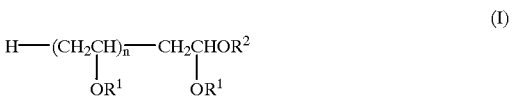

wherein $R^1$, $R^2$, and n are the same as those in the formulae (II) and (III), with hydrogen in the presence of a solid catalyst comprising
  A) rickel in an amount corresponding to 10 to 70% by weight of metallic nickel, and
  B) at least one compound selected from the group consisting of oxides of silicon, aluminum, magnesium, titanium, and zirconium; and synthetic; and natural inorganic oxides containing one or more of these oxides as the constituents thereof.

2. The process for producing an ether compound according to claim 1, wherein the solid catalyst comprises
  (A) nickel in an amount corresponding to 10 to 70% by weight of metallic nickel, and (B) at least one oxide selected from the group consisting of silica, alumina, silica-alumina, magnesia, silica-magnesia, titania, zirconia, zeolite, activated clay, and diatomaceous earth.

3. The process for producing an ether compound according to claim 1, wherein the solid catalyst is selected from the group consisting of nickel-silica-alumina catalysts, nickel-alumina catalysts, nickel-silica-alumina-magnesia catalysts, nickel-zirconia catalysts, and nickel-diatomaceous earth catalysts.

4. The process for producing an ether compound according to claim 1, wherein the one or more acetal compounds are reacted with hydrogen at a temperature of 70 to 200° C.

5. The process for producing an ether compound according to claim 1, wherein the one or more acetal compounds are reacted with hydrogen under a pressure of 3 to 60 kg/cm$^2$.

6. The process for producing an ether compound according to claim 1, wherein the one or more acetal compounds are reacetd with hydrogen continuously in a fixed bed reactor.

7. A process for producing an ether compound according to claim 1, wherein the solid catalyst is packed into a fixed bed reactor, and the one or more acetal compounds are reacted with hydrogen by introducing the acetal compound continuously into the layer of the packed solid catalyst at an LHSV of 0.01 to 10 hr$^{-1}$ in combination with hydrogen to continuously produce the ether compound.

8. The process for producing an ether compound according to claim 1, wherein the one or more acetal compounds are reacted with hydrogen in the presence of the solid catalyst in a suspended condition to produce the ether compound.

9. The process for producing an ether compound according to claim 1, wherein the average molecular weight of the ether compound having the formula (II) or (III) is 150 to 2000.

10. The process for producing an ether compound according to claim 1, wherein the nickel content of the solid catalyst is 15 to 65% by weight.

11. The process for producing an ether compound according to claim 1, wherein R$^1$, and R$^2$ of formula (I), (II) or (III) is a linear or branced C$_1$–C$_8$ alkyl group, or a C$_3$–C$_8$ cycloalkyl group.

12. The process for producing an ether compound according to claim 1, wherein said catalyst is used in an amount of from 0.05 to 20% by weight, based upon the weight of the starting material.

13. The process for producing an ether compound according to claim 1, wherein the number of repeating units in the compound of the formula (II) or (III) is such that either of said compounds has an average molecular weight of about 150 to 2,000.

14. The process for producing an ether compound according to claim 1, wherein the number of repeating units in the compound of the formula (II) or (III) is such that either of said compounds has a kinematic viscosity at 40° C. of about 5 to 1,000 cSt.

15. A process for producing an ether compound according to claim 1, wherein the acetal compound having the formula (I) is a mixture comprising acetal compounds.

16. A process for producing an ether compound according to claim 1, wherein the acetal compound having the formula (I) is mixture containing acetal compounds each having a value of n of 12 or more.

* * * * *

UNITED STATES PATENT AND TRADEMARK OFFICE
CERTIFICATE OF CORRECTION

PATENT NO. : 6,087,539

DATED : July 11, 2000

INVENTOR(S): Hirotaka YAMASAKI, et al.

It is certified that an error appears in the above-identified patent and that said Letters Patent is hereby corrected as shown below:

Column 14, line 57, "A) rickel in" should read --A) nickel in--.

Signed and Sealed this

Twenty-second Day of May, 2001

Attest:

NICHOLAS P. GODICI

Attesting Officer

Acting Director of the United States Patent and Trademark Office